(12) United States Patent
Elangovan

(10) Patent No.: US 8,658,829 B2
(45) Date of Patent: Feb. 25, 2014

(54) METHOD OF PRODUCING POLYALKYLATED OLIGOALKYLENEPOLYAMINES

(75) Inventor: Arumugasamy Elangovan, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 13/522,803

(22) PCT Filed: Feb. 4, 2011

(86) PCT No.: PCT/US2011/023762
§ 371 (c)(1),
(2), (4) Date: Jul. 18, 2012

(87) PCT Pub. No.: WO2011/097490
PCT Pub. Date: Aug. 11, 2011

(65) Prior Publication Data
US 2012/0289748 A1    Nov. 15, 2012

(51) Int. Cl.
*C07C 209/60*    (2006.01)
(52) U.S. Cl.
USPC .......................... 564/481; 564/511; 564/512
(58) Field of Classification Search
USPC ....................................................... 564/481
See application file for complete search history.

(56) References Cited

U.S. PATENT DOCUMENTS

| | | | |
|---|---|---|---|
| 2,638,450 A | 5/1953 | White et al. | |
| 3,324,182 A | 6/1967 | Brunner et al. | |
| 3,472,900 A * | 10/1969 | Dadekian et al. | 564/481 |
| 3,646,147 A * | 2/1972 | Dadekian et al. | 564/386 |
| 3,714,259 A | 1/1973 | Lichtenwalter et al. | |
| 3,755,447 A | 8/1973 | Klemann et al. | |
| 5,166,415 A | 11/1992 | Doumaux et al. | |
| 5,225,598 A | 7/1993 | Doumaux et al. | |

OTHER PUBLICATIONS

Acar et al., Synthesis of Alkylated Linear Amine Ligands and their Effects on Homogenous ATRP, Polymer Preprints, vol. 46(2), pp. 433-434, 2005.
Acar et al., Synthesis of Hexylated Triethylenetetramine: New Ligand for Homogeneous Atom Transfer Radical Polymerization, J. Polym. Sci. Part A: Polym. Chem: vol. 41, pp. 1677-1680, 2003.
International Search Report and Written Opinion for International Application No. PCT/US2011/023762, mail date May 6, 2011, 7 pages.

* cited by examiner

*Primary Examiner* — Brian J Davis
(74) *Attorney, Agent, or Firm* — Foley & Lardner LLP

(57) ABSTRACT

A method of preparing polyalkylated oligoalkylenepolyamines is provided. The method includes contacting oligoalkylenepolyamine with a reagent composition comprising (a) alkyl bromide and/or alkyl chloride; (b) a basic agent; and (c) iodide salt. The alkylation reaction may be carried out in a polar, aprotic organic solvent.

21 Claims, No Drawings

METHOD OF PRODUCING POLYALKYLATED OLIGOALKYLENEPOLYAMINES

GOVERNMENT RIGHTS STATEMENT

This invention was made with government support under U.S. Department of Energy Grant No. DE-FG36-08G088160. The government has certain rights in the invention.

CROSS REFERENCE TO RELATED APPLICATION

This patent application is a U.S. national stage of International Patent Application No. PCT/US2011/023762, filed on Feb. 4, 2011, entitled "Method of Producing Polyalkylated Oligoalkylenepolyamines;" which claims the benefit under 35 U.S.C. 119(e) of U.S. Provisional Application Ser. No. 61/302,408, filed Feb. 8, 2010, entitled "Method of Producing Polyalkylated Oligoalkylenepolyamines," the disclosures of which are herein incorporated by reference in their entirety for any and all purposes.

BACKGROUND

Polyalkylated oligoalkylenepolyamines are useful as ligands in a variety of chemical transformations, e.g., as ligands for metal species in homogeneous atom transfer radical polymerization reactions, and have a variety of other uses, e.g., as anti-wear lubrication additives. Polyalkylated polyamine ligands, such as N,N,N',N'',N''-pentaethyl-diethylenetriamine ("PEDETA") or N,N,N',N'-tetraethylethylenediamine ("TEEDA"), are also useful as ligands in the production of tetradecachlorocyclohexasilane dianions from trichlorosilane. Polyalkylated oligoalkylenepolyamines have commonly been prepared through reaction of polyamine compounds (e.g., dialkylenetriamines) with an alkyl halide. This reaction, however, has been reported to suffer from low yields and/or prolonged reaction times. In many instances, difficulties in inducing the reaction to achieve complete alkylation have been experienced, leading to product mixtures containing substantial amounts of partially alkylated products. Previous attempts to alkylate alkylenepolyamines with 1-chloro-n-alkanes by conventional procedures have resulted in low substitution yield, even after prolonged reaction times. The low conversion rates in such attempted reactions have been attributed to the low reactivity of the alkyl chloride.

SUMMARY

The present application is directed to a method of preparing polyalkylated polyamines. The method results in the formation of polyalkylated polyamine from a oligoalkylenepolyamine. The method includes contacting oligoalkylenepolyamine with a reagent composition comprising (a) alkyl bromide and/or alkyl chloride; (b) a basic agent; (c) iodide salt; and optionally an organic solvent. The alkylation reaction may be carried out in a polar, aprotic organic solvent. In some embodiments, the reaction may be carried out in an organic solvent that includes a lower alcohol.

Examples of suitable polyalkylenepolyamines which may be employed in the present method include diethylenetriamine, dipropylenetriamine, ethylenediamine, propylenediamine, butylenediamine, pentylenediamine, hexylenediamine and triethylenetetraamine. The desired products are typically fully alkylated polyamines, such as pentaalkyldialkylenetriamines, tetraalkylalkylenediamines and hexaalkyltrialkylenetetraamines. For examples, the present method may be used to produce pentaalkyldiethylenetriamines and tetraalkylethylenediamines, such as N,N,N',N'-tetraethylethylenediamine (TEEDA) and pentaethyldiethylenetriamine (PEDETA).

DETAILED DESCRIPTION

The present application relates to a method of forming polyalkylated oligoalkylenepolyamines from alkyl halides and oligoalkylenepolyamines. The reaction comprises contacting the oligoalkylenepolyamine with a reagent composition that includes alkyl halide, a basic agent; and iodide salt. The reaction is typically conducted in the presence of a suitable organic solvent. In some embodiments, the reaction may be carried out in a polar, aprotic organic solvent. In other embodiments, the reaction may be carried out in a solvent that includes a lower alcohol.

In many embodiments, the method relates to forming polyalkylated oligoalkylenepolyamines from alkyl halide and alkylenediamine, dialkylenetriamine or trialkylenetetraamine. For example, the oligoalkylenepolyamine may be an alkylenediamine such as ethylenediamine, propylenediamine, butylenediamine, pentylenediamine or hexylenediamine. The oligoalkylenepolyamine may be a dialkylenetriamine such as diethylenetriamine or dipropylenetriamine. The oligoalkylenepolyamine may be a trialkylenetetraamine such as triethylenetetraamine or tripropylenetetraamine.

The reagent composition comprises an alkyl bromide and/or alkyl chloride. The alkyl bromide and/or alkyl chloride may include $C_2$-$C_{10}$ alkyl, desirably $C_2$-$C_6$ alkyl, commonly ethyl, n-propyl or n-butyl. Examples of suitable alkyl halides for use in the present method include ethyl bromide, n-propyl bromide, n-butyl bromide, n-pentyl bromide, n-hexyl bromide, i-propyl bromide, s-butyl bromide, n-propyl chloride, n-butyl chloride, n-pentyl chloride, and n-hexyl chloride.

The reagent composition comprises a basic agent. Examples of suitable basic agents in presence of which the reaction may be conducted are, e.g., alkali or alkaline earth metal hydroxides or basic salts, such as sodium, potassium, lithium, calcium, barium or magnesium hydroxides, carbonates, acetates, and the like. Alkali or alkaline earth metal carbonates (e.g., $CaCO_3$) are often employed with alkali metal carbonates, such as sodium carbonate ($Na_2CO_3$) and potassium carbonate ($K_2CO_3$), being particularly suitable in many embodiments. The mole ratio of base (e.g., potassium carbonate) to oligoalkylenepolyamine starting material is typically about 2.5-10 moles base per mole of oligoalkylenepolyamine. For example, the reaction may be run using about 5-6 moles $K_2CO_3$ per mole of DETA.

Other suitable examples of basic agents include organic base having a pKa of at least about 11. For example, the organic base may include tertiary amine(s) having a pKa of at least about 11, e.g., where the tertiary amine is substituted with three alkyl and/or aralkyl groups. For example, the basic agent may include an N,N-diisopropylalkylamine and/or an N,N-diisobutylalkylamine, where the alkyl group is methyl, ethyl, n-propyl, isopropyl, n-butyl, s-butyl, and/or other branched/linear alkyl groups (desirably having no more than 6 carbon atoms). The tertiary amine may also be substituted with one or more aralkyl groups, such as a benzyl group and/or phenethyl group. Other examples of suitable tertiary amines include N,N,N',N'-tetraalkyl-1,8-naphalenediamines (e.g., where the alkyl groups are desirably $C_1$-$C_6$ alkyl and preferably methyl) such as N,N,N',N'-tetramethyl-1,8-naphalenediamine and N,N,N',N'-tetraethyl-1,8-naphalenediamine. Other examples of organic bases include nitrogen-containing basic heterocyclic compounds and phosphazenes (also known as aminophosphoranes).

The reagent composition comprises an iodide salt. Examples of suitable iodide salts include alkali metal iodides, e.g., potassium iodide and or sodium iodide. Other examples of suitable iodide salts include tetraalkylammonium iodides, e.g., tetrabutylammonium iodide, and benzyltrialkylammonium iodides, e.g., benzyltrimethylammonium iodide. The amount of iodide salt catalyst (e.g., KI) typically ranges from 0.01-10 mole %, more desirably about 1-5 mole %. Quite commonly about 2 mole % iodide salt catalyst based on oligoalkylenepolyamine (~0.4 mole % based on alkyl halide) is employed.

Although the reaction may be conducted in the absence of a diluent, the present alkylation reaction is typically carried out in the presence of an organic solvent. The organic solvent or mixture of organic solvents is chosen that does not interfere with the reaction of the alkyl halide with the polyamine to form the polyalkylated oligoalkylenepolyamine. When present, the volume of the organic solvent is typically from 0.1 to 100 and often 1 to 10 times the combined volume of the polyalkylenepolyamine and the alkyl halide.

The present N-alkylation reaction is typically carried out in a "polar, aprotic organic solvent," i.e., organic solvent comprising at least one aprotic, polar solvent. As employed herein, the term "polar" as applied to solvents refers to solvents characterized by molecules having sizable permanent dipole moments. The term "aprotic" as applied to solvents refers to a solvent that is incapable of acting as a labile proton donor or acceptor (in contrast to a "protic" solvent, which is capable of acting as a labile proton donor or acceptor). Desirably, the alkylation reaction is carried out in an organic solvent comprising a substantial amount of one or more polar, aprotic solvents, e.g., a solvent including at least about 50 vol. % polar, aprotic solvent(s). Preferably, the alkylation reaction is carried out in a solvent comprising at least about 80 vol. %, more desirably at least about 90 vol. %, and often at least about 95 vol. % polar, aprotic solvent(s), such as N,N-dimethylformamide.

Commonly, the organic solvent may include a polar, aprotic solvent. Examples of suitable polar, aprotic solvents include N,N-dimethylformamide (also referred to as dimethylformamide or DMF), 1-methyl-2-pyrrolidinone (also referred to as N-methyl-2-pyrrolidinone or NMP), N,N-dimethylacetamide (also referred to as dimethylacetamide or DMAc), dimethylsulfoxide (DMSO), hexamethylphosphoramide, and hexamethylphosphorous triamide. Acetonitrile ($CH_3CN$) is another example of a suitable polar, aprotic solvent. Polar, aprotic solvents such as dimethylformamide, dimethylacetamide and/or N-methyl-2-pyrrolidinone are particularly suitable. Quite often, the organic solvent employed is dimethylformamide.

In some embodiments, the present N-alkylation reaction may be carried out in an organic solvent that includes a lower alcohol. Examples of suitable lower alcohols that may be used as a solvent include $C_1$-$C_6$ alcohols, such as $C_1$-$C_4$ alkanols, e.g., ethanol, n-propanol, isopropanol, n-butanol or mixtures thereof.

The present method is preferably carried out under substantially anhydrous conditions. This can be accomplished by purging the reactor with a dry inert gas such as nitrogen or argon and thereafter maintaining a blanket of such inert gas in the reactor. The reaction may also desirably be carried out using a substantially anhydrous solvent, e.g., a solvent (such as DMF and/or DMAc) that has been dried via contact with a desiccating agent, such as anhydrous sodium sulfate ($Na_2SO_4$).

In the present method, the reaction may be conducted in any standard reactor suitable for reaction of a heterogenous mixture containing oligoalkylenepolyamines with another reactant. The reactor can be, for example, a continuous-stirred batch type reactor, semi-batch type reactor, or a continuous type reactor. For example, the reaction may be carried out in a batch type reactor which can be fitted with an overhead stirrer and cooling equipment. Such a reactor may have or optionally be capable of being fitted with a distillation head, thereby allowing components to be distilled directly from the initial crude reaction product mixture.

In the present method, the reaction may suitably be conducted after complete addition of the alkyl halide for reaction times of about 2 hours to 12 hours, typically 3-4 hours. Although the reaction may not require longer than about 3 hours for 0.05 to 0.1 mol scale reaction, a 4× larger scale was also found to require similar reaction time except that the addition of alkyl halide (e.g., bromoethane) and its reflux may require a longer time.

The present alkylation reaction may suitably be carried out at a temperature of from 0° C. to 120° C. Higher temperatures may be employed, often under elevated pressures. Typically, the alkyl halide is initially contacted with the polyalkylenepolyamine at a relatively low temperature, e.g., at a reaction temperature that is below the boiling point of the alkyl halide(s) employed. For example, it may be desirable to conduct the initial stage of the reaction at a reaction temperature that is at least about 20° C. below the boiling point of the alkyl halide(s) being employed. For reactions involving many of the alkyl halides which may be employed in the present alkylation reaction, this may be a temperature of about −10° C. to 50° C. The particular temperature selected will depend on the nature of the alkyl halide reactant, e.g., reactions employing ethyl bromide as the alkyl halide will typically be carried out at an initial temperature below room temperature, e.g., below about 20° C., while reactions involving higher molecular weight alkyl bromides (e.g., n-propyl bromide, n-propyl chloride, n-butyl bromide, n-butyl chloride, n-pentyl bromide, n-pentyl chloride, n-hexyl bromide and/or n-hexyl chloride) may be conducted at higher initial temperatures.

The polyalkylated oligoalkylenepolyamine product may be recovered from the reaction product mixture by conventional techniques. For example, in some instances the crude reaction product mixture may simply be subjected to vacuum distillation, first to remove solvent and unreacted alkyl halide and then subsequently to isolate a purified product stream that contains a high percentage of fully alkylated polyamine (desirably at least about 95 wt. % and preferably a product stream that contains at least about 98 wt. % fully alkylated polyamine).

In some embodiments, the crude reaction product mixture may be subjected to distillation to remove solvent and unreacted alkyl halide. The resulting residue, a mixture comprising alkylated polyamine and inorganic salts as the primary components, may then be separated via partitioning between aqueous and organic phases, e.g., by partitioning between water and ethyl acetate phases. After separation and drying of the organic (ethyl acetate) phase, solvent may be removed from the recovered material and the residual polyamine fraction may be purified, e.g., by vacuum distillation.

The following examples are presented to illustrate the present invention and to assist one of ordinary skill in making and using the same. The examples are not intended in any way to otherwise limit the scope of the invention. All percentages are by weight unless otherwise noted.

EXAMPLE 1

Synthesis of pentaethyldiethylenetriamine (PEDETA)

A three-necked round-bottomed flask (3 L) equipped with a Friedrich's condenser and an overhead mechanical stirrer was placed in a cooling bath. The flask was charged with dimethylformamide (DMF, 600 mL), potassium carbonate (348 g), and potassium iodide (23 g). The mixture was allowed to stir until the potassium iodide was dissolved (giving a faint yellow tint) and the potassium carbonate was fairly homogenized. Diethylenetriamine (52 g) was then added. Bromoethane (300 g) was added drop-wise to the resulting reaction mixture from a pressure-equalizing addition funnel under efficient mechanical stirring. An exothermic reaction occurred with the refluxing of bromoethane (chiller temperature ~5° C.). After all the bromoethane had been added and the exotherm subsided, the cooling bath was replaced by a heating mantle or oil bath. The reaction mixture was then set to reflux (~40° C. reaction temperature; ~60° C. bath temperature) under efficient stirring. After refluxing overnight, the reaction set-up was modified for vacuum distillation and a majority of the DMF (about 450 mL). The pasty solid remaining back in the reaction flask was partitioned between water and ethyl acetate in a separatory funnel to extract the product PEDETA from the inorganic salts. The aqueous solution was extracted three times and the combined ethyl acetate solutions were washed with water and brine solution. The ethyl acetate extract was dried over sodium sulfate, filtered and concentrated using a rotary evaporator. The oily residue obtained was distilled under reduced pressure to isolate a pure fraction of PEDETA (61-82 g).

EXAMPLE 2

Synthesis of tetrabutylethylenediamine

A three-necked round-bottomed flask (3 L) equipped with a Friedrich's condenser and an overhead mechanical stirrer is placed in a cooling bath. The flask is charged with dimethylformamide (DMF, 500 mL), potassium carbonate (2.1 mol), and potassium iodide (0.1 mol). The mixture is allowed to stir until the potassium iodide was dissolved (giving a faint yellow tint) and the potassium carbonate was fairly homogenized. Ethylenediamine (0.5 mol) is then added to the reaction mixture. 1-Chlorobutane (2.2 mol) is added drop-wise to the resulting reaction mixture from a pressure-equalizing addition funnel under efficient mechanical stirring. During the addition of the alkyl halide, the exothermic reaction which may occur is controlled by cooling the round-bottomed flask bath with the cooling bath so as to maintain the reaction temperature below room temperature (e.g., using a chiller temperature ~5° C.). After all the alkyl halide has been added and any exotherm subsides, the cooling bath is replaced by a heating mantle or oil bath. The reaction mixture is then heated (~50° C. reaction temperature; ~70-80° C. bath temperature) under efficient stirring. After heating overnight, the reaction set-up is modified for vacuum distillation and unreacted alkyl halide and a majority of the DMF (about 400-450 mL) is removed. The resulting residual mixture in the reaction flask is partitioned between water and ethyl acetate in a separatory funnel to separate the polyalkylated product from the inorganic salts. The aqueous fraction is extracted three times with ethyl acetate and the combined ethyl acetate solutions are sequentially washed with water and brine solution. The ethyl acetate extract is dried over sodium sulfate, filtered and concentrated using a rotary evaporator. The resulting oily residue can be distilled under reduced pressure to isolate a purified fraction of tetrabutylethylenediamine.

EXAMPLE 3

Synthesis of pentapropyldipropylenetriamine

A three-necked round-bottomed flask (3 L) equipped with a Friedrich's condenser and an overhead mechanical stirrer is placed in a cooling bath. The flask is charged with dimethylformamide (DMF, 500 mL), potassium carbonate (2.6 mol), and potassium iodide (0.1 mol). The mixture is allowed to stir until the potassium iodide was dissolved (giving a faint yellow tint) and the potassium carbonate was fairly homogenized. Dipropylenetriamine (0.5 mol) is then added to the reaction mixture. 1-Bromopropane (2.7 mol) is added drop-wise to the resulting reaction mixture from a pressure-equalizing addition funnel under efficient mechanical stirring. During the addition of the alkyl halide, the exothermic reaction which may occur is controlled by cooling the round-bottomed flask bath with the cooling bath so as to maintain the reaction temperature below room temperature (e.g., using a chiller temperature ~5° C.). After all the alkyl halide has been added and any exotherm subsides, the cooling bath is replaced by a heating mantle or oil bath. The reaction mixture is then heated (~40° C. reaction temperature; ~60° C. bath temperature) under efficient stirring. After heating overnight, the reaction set-up is modified for vacuum distillation and unreacted alkyl halide and a majority of the DMF (about 400-450 mL) is removed. The residual mixture in the reaction flask is partitioned between water and ethyl acetate in a separatory funnel to separate the polyalkylated product from the inorganic salts. The aqueous fraction is extracted three times with ethyl acetate and the combined ethyl acetate solutions are sequentially washed with water and brine solution. The ethyl acetate extract is dried over sodium sulfate, filtered and concentrated using a rotary evaporator. The resulting oily residue can be distilled under reduced pressure to isolate a purified fraction of pentapropyldipropylenetriamine.

EXAMPLE 4

Synthesis of hexaethyltriethylenetetraamine

A three-necked round-bottomed flask (3 L) equipped with a Friedrich's condenser and an overhead mechanical stirrer is placed in a cooling bath. The flask is charged with dimethylacetamide (DMAc, 500 mL), potassium carbonate (3.1 mol), and potassium iodide (0.15 mol). The mixture is allowed to stir until the potassium iodide was dissolved (giving a faint yellow tint) and the potassium carbonate was fairly homogenized. Triethylenetetraamine (0.5 mol) is then added to the reaction mixture. 1-Bromoethane (3.25 mol) is added drop-wise to the resulting reaction mixture from a pressure-equalizing addition funnel under efficient mechanical stirring. During the addition of the alkyl halide, the exothermic reaction which may occur is controlled by cooling the round-bottomed flask bath with the cooling bath so as to maintain the reaction temperature below room temperature (e.g., using a chiller temperature ~5° C.). After all the alkyl halide has been added and any exotherm subsides, the cooling bath is replaced by a heating mantle or oil bath. The reaction mixture is then heated (~40° C. reaction temperature; ~60° C. bath temperature) under efficient stirring. After heating overnight, the reaction set-up is modified for vacuum distillation and unreacted alkyl halide and a majority of the DMAc (about 400-450 mL) is removed. The residual mixture in the reaction flask is partitioned between water and ethyl acetate in a separatory funnel to separate the polyalkylated product from the inorganic salts. The aqueous fraction is extracted three times with ethyl acetate and the combined ethyl acetate solutions are sequentially washed with water and brine solution. The ethyl acetate extract is dried over sodium sulfate, filtered and concentrated using a rotary evaporator. The resulting oily residue can be distilled under reduced pressure to isolate a purified fraction of hexaethyltriethylenetetraamine.

EXAMPLE 5

Synthesis of 1,1,4,7,7-pentaethyldiethylenetriamine (PEDETA)

The following is a description of an illustrative procedure for conducting the present method for making PEDETA. The method allows the efficient production of the desired product with little or no formation of partially alkylated triamine sideproducts, e.g., 1,1,7,7-tetraethyldiethylene-triamine ($Et_2N$—$(CH_2)_2$—NH—$(CH_2)_2$—$NEt_2$, TEDETA). The following scheme describes the reaction as run in this example:

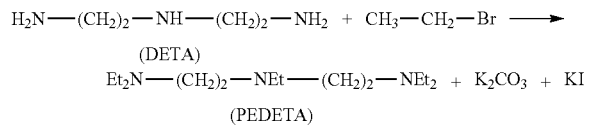

A 500 mL three-necked round-bottomed flask equipped with a mechanical stirrer and Friedrich's condenser was charged with DETA (8.2 mL; 0.076 mol) and 120 mL of DMF solvent. The DETA is desirably a grade which is clear and colorless. The total amount of DMF may be added as a single aliquot or the solvent can be split into smaller amounts and added into the reaction mixture at stages where washing down the funnels, lines, etc., into the reaction mixture is advantageous. The resulting mixture was set to stir mechanically and KI (0.252 g; 0.0015 mol; 2 mol % based on DETA), which is preferably be ground into a fine powder before addition, was added. The KI dissolved slowly into the mixture. When dissolution was nearly complete, bromoethane (35 mL; 0.46 mol) was added using an addition funnel through the third neck under stirring. This addition was at such a rate that an exotherm was noticed and the reaction mixture turned opaque with the formation white crystals. An ice-water bath may be used to control the exotherm, if necessary. A loss of yield may be observed if the exotherm is either not observed (due to excessive cooling—lowering the activation of reaction) or not controlled resulting in the evaporation of bromoethane. After all the bromoethane was added, the white crystals dissolved and the color of the reaction solution turned yellow/orange.

After some time, the addition funnel was replaced with a powder funnel and the basic $K_2CO_3$ (63.5 g; 0.46 mol) was quickly added as a single lot into the reaction mixture under stirring and the funnel was replaced with a greased stopper. The $K_2CO_3$ is preferably added as a fine powder rather than in the coarser original commercial form. The reaction mixture was then heated to about 60° C. (bath/mantle temperature). Refluxing of the mixture was noticed at the beginning but stopped after about two hours. For larger scale reaction, this time duration may be somewhat longer. The reaction mixture was then continuously heated under efficient stirring for an additional hour.

A small aliquot of the reaction mixture (about 0.5 mL) was drawn from the reaction mixture and partitioned in a vial tube with ether (about 0.5-1 mL) and water (about 3-5 mL). The ether fraction was separated and the ether evaporated. The resulting oily residue was dissolved in appropriate solvent for gas chromatographic (methylene chloride) and for $^1$H-NMR ($CDCl_3$) spectral analyses. The crude reaction mixture was found to contain the desired PEDETA as the major component along with small amount of DMF and extraction solvent(s). None of the partial alkylation product, TEDETA, was observed from these data. Under the conditions of the gas chromatographic analysis that was employed, a PEDETA peak appeared at a retention time of 12 minutes while that for TEDETA, if present, would have appeared at a retention time of 11 minutes.

The bulk reaction mixture was then filtered to remove inorganic salts, which were washed with ethyl acetate. The combined filtrate was partitioned between water and ethyl acetate. Ethyl acetate and ether both work well as extracting solvents; ethyl acetate typically extracts more product from the aqueous phase but it also extracts more DMF into the organic phase. While ether extracts less DMF, it also tends to leave some of the PEDETA product in the aqueous layer. The organic solution was dried over anhydrous sodium sulfate and then passed through a silica gel plug. The dried filtrate was evaporated using a rotavapor to provide a clear and nearly colorless oily crude product. The crude product was distilled under reduced pressure (70-73° C./50-100 mTorr). $^1$H-NMR data ($CDCl_3$, δ ppm): 1.02 (m, 15 H), 2.54 (m 18 H); MS m/z: 86 (100%), 100, 157. The yield for several attempts on this scale ranged from 50-68%, with a yield of about 55% PEDETA being commonly afforded on this scale.

When the reaction is run on larger scales it may be beneficial to modify the work-up process as follows: After the required period of heating the reaction mixture, the reaction flask is cooled to room temperature and ether and/or ethyl acetate is added to the mixture in order to dilute the DMF and encourage precipitation of most inorganics. Then the diluted mixture is filtered and the filtrate is passed through a silica gel plug of appropriate size. The filtrate thus collected is concentrated on a rotary evaporator to remove ether/ethyl acetate and the remaining solution of the product in DMF fractionally distilled under reduced pressure. Thus, DMF is distilled off first at about 25-30° C. at 500 mTorr, and then the product PEDETA is recovered at 75-80° C. at about 200 mTorr (or, at 65-70° C. at about 80-100 mTorr). This approach can simplify the work-up process and help avoid the loss of product yield in aqueous solutions.

Illustrative Embodiments

Reference is made in the following to a number of illustrative embodiments of the subject matter described herein. The following embodiments illustrate only a few selected embodiments that may include the various features, characteristics, and/or advantages of the subject matter as presently described. Accordingly, the following embodiments should not be considered as being comprehensive of all of the possible embodiments.

According to one embodiment, a polyalkylated oligoalkylenepolyamine is produced by a method comprising contacting an oligoalkylenepolyamine with a reagent composition comprising:
  (a) alkyl bromide and/or alkyl chloride;
  (b) a basic agent; and
  (c) iodide salt.

The oligoalkylenepolyamine may be contacted with the reagent composition in the presence of a solvent, such as a polar, aprotic organic solvent. The polar, aprotic organic solvent may comprise dimethylformamide, dimethylacetamide and/or N-methyl-2-pyrrolidinone. Examples of suitable polar, aprotic organic solvent include polar, aprotic solvents which contain at least about 90 vol. % dimethylformamide or at least about 90 vol. % dimethylacetamide. In some instances, the solvent may comprise a lower alcohol, such as a $C_1$-$C_4$ alkanol, e.g., ethanol, n-propanol, isopropanol and/or n-butanol.

In some embodiments, the alkyl groups in the alkyl bromide and/or alkyl chloride may be $C_2$-$C_{10}$ alkyl, desirably $C_2$-$C_6$ alkyl, commonly ethyl or n-propyl groups.

In some embodiments, the basic agent comprises carbonate salt. For example, the basic agent may comprise potassium carbonate, sodium carbonate and/or calcium carbonate. In some embodiments, the basic agent may comprise alkali metal carbonate, e.g., sodium carbonate and/or potassium carbonate. The basic agent comprises an organic base having a pKa of at least about 11. In some embodiments, the basic agent may comprise an organic base, such as a sterically hindered amine, e.g., N,N-diisopropylethylamine.

In some embodiments, the iodide salt may comprise alkali metal iodide, sodium iodide and/or potassium iodide.

In some embodiments, the basic agent comprises potassium carbonate; the iodide salt comprises potassium iodide; and the reagent composition comprises alkyl bromide in which the alkyl group is $C_2$-$C_4$ n-alkyl group. In other embodiments, the basic agent comprises potassium carbonate; the iodide salt comprises potassium iodide; and the reagent composition comprises alkyl chloride in which the alkyl group is $C_3$-$C_6$ n-alkyl group.

In some embodiments, the oligoalkylenepolyamine is an alkylenediamine, dialkylenetriamine or trialkylenetetraamine. The alkylenediamine may be ethylenediamine, propylenediamine, butylenediamine, pentylenediamine or hexylenediamine. The dialkylenetriamine may be diethylenetriamine or dipropylenetriamine. The trialkylenetetraamine may be triethylenetetraamine or tripropylenetetraamine.

In some embodiments, the polyalkylated oligoalkylenepolyamine formed in the reaction may be a pentaalkyldialkylenetriamine, e.g., a pentaalkyldiethylenetriamine or pentaalkyldipropylenetriamine. In other embodiments, the polyalkylated oligoalkylenepolyamine formed in the reaction may be a tetraalkylalkylenediamine, e.g., a tetraalkylethylenediamine (e.g., N,N,N',N'-tetraethylethylenediamine (TEEDA)) or a tetraalkylpropylenediamine. In other embodiments, the polyalkylated oligoalkylenepolyamine formed in the reaction may be a penta-(n-alkyl)-diethylenetriamine and/or tetra-(n-alkyl)-ethylenediamine, e.g., N,N,N',N'',N''-pentaethyldiethylenetriamine (PEDETA). In other embodiments, the polyalkylated oligoalkylenepolyamine formed in the reaction may be a penta-(n-alkyl)-dipropylenetriamine or tetra-(n-alkyl)-propylenediamine.

In some embodiments, a polyalkylated oligoalkylenepolyamine is produced by a method comprising (a) forming a first mixture comprising oligoalkylenepolyamine; a basic agent; iodide salt; and polar, aprotic organic solvent;

(b) adding alkyl bromide and/or alkyl chloride to the first mixture to form a second mixture; and (c) heating the second mixture for several hours (e.g., 2 to 24 hours, desirably at least about 5 to 10 hours) to form a crude reaction product mixture.

The alkyl bromide and/or alkyl chloride may be added to the first mixture in a dropwise manner to form a second mixture. Typically, the alkyl bromide and/or alkyl chloride is added to the first mixture at a rate that maintains the reaction temperature at about 50-100° C. Certain embodiments may further comprise subjecting the crude reaction product mixture to distillation to remove at least a portion of unreacted alkyl halide and/or polar, aprotic organic solvent, thereby forming a distillation residue. Certain embodiments may further comprise subjecting the distillation residue to vacuum distillation to provide a purified polyalkylated oligoalkylenepolyamine fraction.

In some embodiments, the crude reaction product mixture may be cooled to room temperature (about 25° C.) and then diluted with a second solvent to encourage precipitation of a large portion of the inorganic components present. The second solvent may suitably be an aliphatic ether or ester, e.g., dialkyl ether, cyclic ether and/or alkyl acetate, such as diethyl ether, tetrahydrofuran and/or ethyl acetate. The diluted reaction product mixture may then be filtered to provide a product filtrate. The product filtrate can be further purified, e.g., via vacuum distillation as described above, if desired.

Certain embodiments may further comprise separating the distillation residue between an aqueous stream and an organic (e.g., non-chlorinated solvents such as ethyl acetate and/or diethyl ether) stream. Certain embodiments may further comprise removing solvent from the organic stream to provide a polyamine-enriched residue. Certain embodiments may further comprise distilling the polyamine-enriched residue to provide a purified polyalkylated oligoalkylenepolyamine fraction.

It will be readily apparent to one skilled in the art that varying substitutions and modifications may be made to the methods and compositions disclosed herein without departing from the scope and spirit of the invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

What is claimed is:

1. A method of preparing a polyalkylated oligoalkylenepolyamine comprising:
    contacting oligoalkylenepolyamine with a reagent composition comprising:
    (a) alkyl bromide, alkyl chloride or a mixture thereof;
    (b) a basic agent; and
    (c) iodide salt;
    wherein contacting the oligoalkylenepolyamine with the reagent composition is conducted in the presence of a polar, aprotic organic solvent.

2. The method of claim 1 wherein the alkyl groups in the alkyl bromide and/or alkyl chloride are ethyl or n-propyl.

3. The method of claim 1 wherein the basic agent comprises carbonate salt.

4. The method of claim 1 wherein the iodide salt comprises alkali metal iodide.

5. A method of preparing a polyalkylated oligoalkylenepolyamine comprising:
   contacting oligoalkylenepolyamine with a reagent composition comprising:
   (a) C2-C4n-alkyl bromide, C3-C6n-alkyl chloride or a mixture thereof;
   (b) a basic agent which comprises alkali metal carbonate; and
   (c) an iodide salt which comprises alkali metal iodide.

6. The method of claim I wherein basic agent comprises alkali metal carbonate; the iodide salt comprises alkali metal iodide; and the reagent composition comprises alkyl chloride in which the alkyl group is $C_3$-$C_6$n-alkyl group.

7. The method of claim 5 wherein the oligoalkylenepolyamine is an alkylenediamine, dialkylenetriamine or trialkylenetetraamine.

8. The method of claim 1 wherein the polyalkylated oligoalkylenepolyamine is a pentaalkyldiethylenetriamine, a tetraalkylethylenediamine, a tetraalkylpropylenediamine or a pentaalkyldipropylenetriamine.

9. The method of claim 5 wherein the polyalkylated oligoalkylenepolyamine is N,N,N',N'',N''-pentaethyldiethylenetriamine or N,N,N',N'-tetraethyl-ethylenediamine.

10. The method of claim 1 wherein contacting the oligoalkylenepolyamine with the reagent composition is conducted in the presence of the polar, aprotic organic solvent and a lower alcohol.

11. The method of claim 1 wherein the basic agent comprises an organic base having a pKa of at least about 11.

12. A method of preparing a polyalkylated oligoalkylenepolyamine comprising:
   (a) forming a first mixture comprising oligoalkylenepolyamine; a basic agent; iodide salt; and a polar, aprotic organic solvent;
   (b) adding alkyl bromide and/or alkyl chloride to the first mixture to form a second mixture; and
   (c) heating the second mixture to form a crude reaction product mixture.

13. The method of claim 12 further comprising distilling the crude reaction product mixture to remove at least a portion of unreacted alkyl halide and/or polar, aprotic organic solvent and provide a first distillation residue.

14. The method of claim 13 further comprising partitioning the first distillation residue between an aqueous stream and an organic stream.

15. The method of claim 14 further comprising removing solvent from the organic stream to provide a polyamine-enriched residue; and distilling the polyamine-enriched residue to provide a distilled polyalkylated oligoalkylenepolyamine fraction.

16. The method of claim 13 further comprising vacuum distilling the distillation residue to provide a distilled polyalkylated oligoalkylenepolyamine fraction.

17. The method of claim 12 further comprising cooling the crude reaction product mixture; diluting the cooled crude reaction product with a second solvent; filtering the diluted crude reaction product to remove inorganic components and provide a polyalkylated polyamine-enriched fraction; and distilling the polyalkylated polyamine-enriched fraction to provide a distilled polyalkylated oligoalkylenepolyamine fraction.

18. The method of claim 1 wherein the iodide salt comprises tetraalkylammonium iodide or benzyltrialkylammonium iodide.

19. The method of claim 18 wherein the reagent composition comprises alkyl chloride, which includes an C3-C6n-alkyl group;
   the oligoalkylenepolyamine is ethylenediamine, diethylenetriamine or triethylenetetraamine; and
   the basic agent comprises alkali metal carbonate.

20. The method of claim 5 wherein contacting the oligoalkylenepolyamine with the reagent composition comprises contacting the oligoalkylenepolyamine with the reagent composition in the presence of a solvent which includes a polar, aprotic organic solvent.

21. The method of claim 12 wherein the oligoalkylenepolyamine is an alkylenediamine, dialkylenetriamine or trialkylenetetraamine;
   the basic agent comprises alkali metal carbonate;
   the iodide salt comprises alkali metal iodide;
   the alkyl bromide is a C2-C4n-alkyl bromide; and
   the alkyl chloride is a C3-C6n-alkyl chloride.

* * * * *